(12) United States Patent
VanOsdol et al.

(10) Patent No.: US 6,672,725 B1
(45) Date of Patent: Jan. 6, 2004

(54) TRANSPIRATION PURGED OPTICAL PROBE

(75) Inventors: John VanOsdol, Fairmont, WV (US); Steven Woodruff, Morgantown, WV (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/040,747

(22) Filed: Jan. 9, 2002

(51) Int. Cl.$^7$ .................................................. G02B 1/00
(52) U.S. Cl. ...................... 359/509; 359/507; 359/896; 356/241.1
(58) Field of Search ........................... 356/241.1, 241.5, 356/241.6, 436, 437; 359/896, 507, 508, 509, 510, 511, 512, 513, 514; 73/23.37, 23.4, 61.48, 61.69

(56) References Cited

U.S. PATENT DOCUMENTS 4,738,528 A * 4/1988 Craft ........................... 356/43
5,115,342 A * 5/1992 Rowe et al. ................. 359/509

\* cited by examiner

*Primary Examiner*—Drew Dunn
*Assistant Examiner*—Joshua L Pritchett
(74) *Attorney, Agent, or Firm*—Bradley W. Smith; Mark P. Dvorscak; Paul A. Gottlieb

(57) ABSTRACT

An optical apparatus for clearly viewing the interior of a containment vessel by applying a transpiration fluid to a volume directly in front of the external surface of the optical element of the optical apparatus. The fluid is provided by an external source and transported by means of an annular tube to a capped end region where the inner tube is perforated. The perforation allows the fluid to stream axially towards the center of the inner tube and then axially away from an optical element which is positioned in the inner tube just prior to the porous sleeve. This arrangement draws any contaminants away from the optical element keeping it free of contaminants. In one of several embodiments, the optical element can be a lens, a viewing port or a laser, and the external source can provide a transpiration fluid having either steady properties or time varying properties.

12 Claims, 2 Drawing Sheets

TRANSPIRATION PURGED OPTICAL PROBE

The United States Government has rights in this invention pursuant to the employer-employee relationship of the U.S Department of Energy and the inventors as U.S. Department of Energy employees at the National Energy Technology Laboratory.

BACKGROUND OF THE INVENTION

This invention relates to a type of optical apparatus for use in a containment vessel or chamber. The apparatus is capable of maintaining its external optical surface free from dust and other contaminants which could effect the clarity of the optical image coming from inside the containment chamber. When an optical probe is used in conjunction with a containment vessel hazardous materials often make maintaining a clean optical surface difficult, and the lack of a clean surface results in a reduction, to varying degrees, of the amount of light passing through the lens or other optical instrument. This device employs a distinct fluid flow pattern to maintain optical clarity and can be used in a gas or liquid environment, and the contaminants can be in the form of either a gas, liquid or solid.

The subject apparatus employs the use of an inert transpiration fluid to keep the optics free from surface contamination. This fluid is dispersed in a symmetrical manner in front of the exposed optical surface to form an optical purge. The purge functions to keep the optical surface clean and thus, free from contaminants which allows for clear viewing. This is accomplished by providing a transpiration fluid from a source outside the containment vessel and flowing the fluid through an annulus formed by the use of two concentric tubes leading to a porous opening located directly in front of the optical lens which is located in the contamination chamber. The temperature, pressure, and flow rate of the transpiration fluid are controlled using apparatus located outside the containment vessel. These fluid properties can be varied to provide for optimum conditions relative to the type of contaminants and the conditions present in the containment vessel. This ability to control the temperature, pressure and flow rate of the transpiration fluid allow the operator to provide a transpiration fluid having steady physical properties, or in the case where the conditions in the containment vessel are changing, a transpiration fluid having variable properties to allow the fluid properties to match the conditions in the containment vessel in a time varying manner.

Once the fluid exits the tubular annulus through the porous cylindrical sleeve, it is positioned directly in front of the optical surface. This arrangement causes the fluid to flow radially inward and then axially away from the optical surface. This pattern of flow by the transpiration fluid prevents any dust or other contaminants which are floating in the vessel from depositing on the optical surface and restricting its imaging capability; this is accomplished by producing a fluid flow which is directed axially away from the center of the optical surface. With this apparatus, the transpiration fluid can be either a liquid or a gas.

Other devices which use discrete orifices in an attempt to keep the optical surface clean tend to entrain contaminants and carry them to the vicinity of the optical surface.

Thus, it is an object of this invention to provide an apparatus for keeping the optical surface associated with an optical probe free of contaminants, A further object of this invention is to provide an apparatus in which the transpiration fluid can be either a liquid or a gas depending on the substance contained in the containment vessel.

Additional advantages, objects and novel features of the invention will become apparent to those skilled in the art upon examination of the following and by practice of the invention.

SUMMARY OF THE INVENTION

This invention comprises an apparatus for keeping the exposed optical surface of an optical probe free of contaminants when it is positioned in a containment vessel. The apparatus directs a transpiration fluid down a cylindrical annulus to a porous inner cylindrical sleeve which then directs the transpiration fluid radially inward towards the central axis of the optical surface, thus, keeping the surface free from the depositions of contaminants on its surface. With this apparatus, either a liquid or a gas can be used as the transpiration fluid and the temperature and pressure of the fluid controlled to provide for either steady conditions or time varying conditions.

BRIEF DESCRIPTION OF THE DRAWINGS

The present invention is illustrated in the accompanying drawings where.

DETAILED DESCRIPTION OF THE INVENTION

Figure 1:
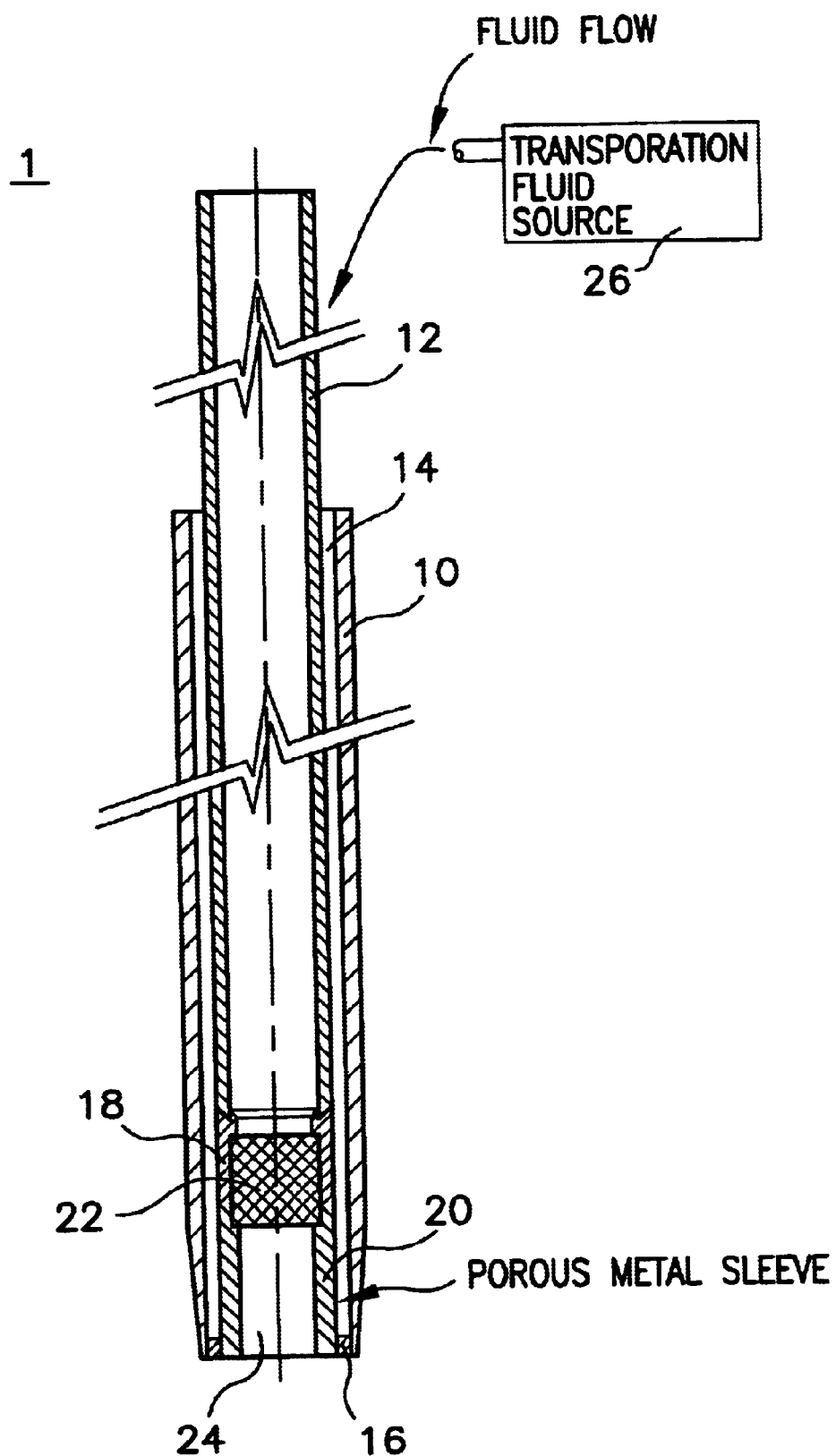
FIG. 1 depicts an axial cross section of the tip of an optical probe employing a passive optical access.

FIG. 1 depicts a transpiration probe 1 for keeping the optical surface of an optical probe free from the deposition of contaminants when the probe is used in an environment containing contaminants which could impair the optical capability of the probe. The apparatus consists of an outer tube 10 enclosing a inner tube 12 of lesser diameter to form a cylindrical annulus 14 which provides a passage for directing the flow of a transpiration fluid. The cylindrical annulus is capped by a ring 16 which provides a barrier for the further flow of the transpiration fluid down the cylindrical annulus 14, In the case of FIG. 1, a stainless steel ring is used, however, any inert material could be used. The annulus 14 is connected to an outer source 26 having the capability of adjusting the temperature and pressure of the fluid leaving the source and thus, being able to supply the transpiration fluid at a given temperature, pressure, and flow rate to the surface of the optical element 22. The source 26 is capable of maintaining these physical properties of the transpiration fluid in a steady state condition or in a time varying condition where the variation of the physical properties of the fluid can be coordinated or linked to the properties internal to the containment vessel. The end portion of the inner tube 12 is segmented into two distinct parts 18 and 20. These parts 18 and 20 serve to retain an optical element 22 in the correct position away from the end of the tube 12. In addition, the end portion of section 20 is porous to allow the transpiration fluid to flow into the central area 24 of the end of the inner tube. Since the perforation segment or sleeve 20 involves the entire tube element, this provides for a more or less uniform pattern offluid flow around the entire circumference and allows for a symmetric flow pattern into the center 24 of end segment 20 with a resulting axial flow away from the optical element 22 which can be a lens or some other light transmitting unit such as a glass or plastic viewing port.

Figure 2:
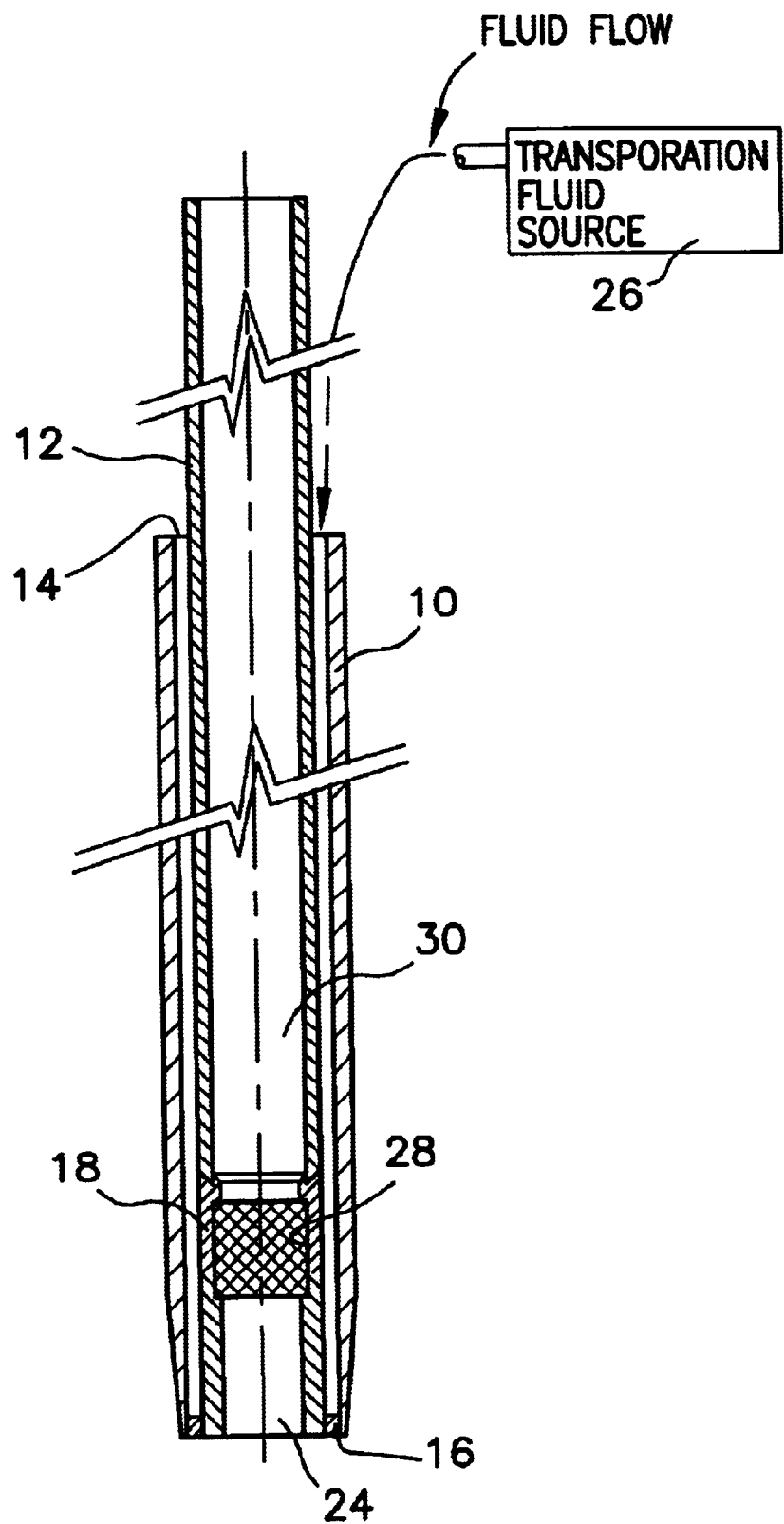
FIG. 2 depicts an axial cross section of the tip of an optical probe where the optical access is a laser.

FIG. 2 depicts a system where the optical element 28 is now the exit port for a laser 30. In this configuration, the elements of the remainder of the probe 1 remain the same as in FIG. 1.

The foregoing description of a preferred embodiment of the invention has been presented for purposes of illustration and description. It is not intended to be exhaustive or to limit the invention to the precise form disclosed, and obviously many modifications and variations are possible in light of the above teaching. The embodiments described explain the principles of the invention and practical applications and should enable others skilled in the art to utilize the invention in various embodiments and with various modifications as are suited to the particular use contemplated. It is intended that the scope of the invention be defined by the claims appended hereto.

What is claimed is:

1. An optical probe for improved viewing of the interior of a containment chamber comprising:

an inner cylindrical tube having an inner tube diameter, an inner tube length and an inner tube end face;

an outer cylindrical tube having a specified outer tube diameter and an outer tube length where said outer tube diameter is greater than said inner tube diameter, where said outer tube encloses said inner tube to form a cylindrical annulus between an outer surface of said inner tube and an inner surface of said outer tube;

an end tube coupling system where a coupling face of said end tube system joins with said inner tube end face to create a coupling face and where a cylindrical length of said end tube system is scaled such that a combined length of said inner tube and said end tube system approximately equals said length of said outer tube and where a porous cylindrical length of tube which is part of said end tube coupling system and which is positioned in opposition to said coupling face and extends from an outer end of said tube system towards said coupling face and is symmetrically perforated to allow a fluid to pass from said annulus to a cylindrical volume formed by cylindrical inner face of said end tube system where said fluid initially experiences a generally radial flow which turns axial as a central axis of said cylindrical volume is approached;

a capping device which seals said annulus at a position approximating an outer tube end face of said outer tube and an end face of said tube system;

an optical means for providing an optical access to the interior of the containment vessel where said optical means is positioned interior to said inner tube and at a position within said end tube coupling system in a region exclusive of perforation and acts to direct the axial motion of the fluid along said central axis in a direction opposed to said optical means;

a fluid coupling system which couples said annulus to an external fluid source which provides a transpiration fluid to said annulus.

2. The apparatus of claim 1 where said end tube coupling system consists of a first tube having said coupling face at one end and a second end face at the other and a second tube having a third face which abuts against said second face of said first tube.

3. The apparatus of claim 2 where said second face and said third face are machined to accept said optical means.

4. The apparatus of claim 3 where said optical means is a lens.

5. The apparatus of claim 3 wherein said optical means is a viewing port.

6. The apparatus of claim 3 wherein said optical means is a laser beam exit port.

7. The apparatus of claim 1 where said porous portion provides for perforations which completely encircle said tube providing for a symmetrical radial flow of said transpiration fluid.

8. The apparatus of claim 1 where said fluid is a gas.

9. The apparatus of claim 1 where said fluid is a liquid.

10. The apparatus of claim 1 where said fluid source provides said fluid at a specified flow rate such that said fluid passes through said length of porous tube or porous sleeve at such a rate and pressure as to keep said optical means free of contamination.

11. The apparatus of claim 10 wherein said fluid source is capable of providing said fluid at a steady fluid flow rate or a time varying flow rate.

12. The apparatus of claim 1 where said fluid source provides said fluid at a specific temperature.

* * * * *